United States Patent [19]

Saito et al.

[11] Patent Number: 5,142,187
[45] Date of Patent: Aug. 25, 1992

[54] PIEZOELECTRIC COMPOSITE TRANSDUCER FOR USE IN ULTRASONIC PROBE

[75] Inventors: Koetsu Saito, Tokyo; Masami Kawabuchi, Yokohama, both of Japan

[73] Assignee: Matsushita Electric Industrial Co., Ltd., Japan

[21] Appl. No.: 394,458

[22] Filed: Aug. 16, 1989

[30] Foreign Application Priority Data

Aug. 23, 1988 [JP] Japan ................. 63-208721

[51] Int. Cl.⁵ .............................. H01L 41/08
[52] U.S. Cl. .................... 310/358; 310/334; 310/337; 501/82
[58] Field of Search ............... 310/357-359, 310/800, 334, 337; 29/25.35; 501/82

[56] References Cited

U.S. PATENT DOCUMENTS

| | | | |
|---|---|---|---|
| 2,831,175 | 4/1958 | Janssen et al. | 310/337 X |
| 2,961,636 | 11/1960 | Benecke | 310/337 X |
| 3,854,060 | 12/1974 | Cook | 310/337 X |
| 4,227,111 | 10/1980 | Cross et al. | 310/358 |
| 4,412,148 | 10/1983 | Klicker et al. | 310/357 X |
| 4,422,003 | 12/1983 | Safari et al. | 310/358 |
| 4,613,784 | 9/1986 | Haun et al. | 310/358 |
| 4,683,396 | 7/1987 | Takeuchi et al. | 310/358 |
| 4,686,409 | 8/1987 | Kaarmann et al. | 310/358 |
| 4,728,845 | 3/1988 | Haun et al. | 310/357 X |
| 4,751,013 | 6/1988 | Kaarmann et al. | 501/82 X |
| 4,751,419 | 6/1988 | Takahata | 310/324 |
| 4,572,981 | 2/1986 | Zola | 310/358 X |
| 4,777,153 | 10/1988 | Sonuparlak | 501/82 |
| 4,928,264 | 5/1990 | Kahn | 310/800 X |
| 4,933,230 | 6/1990 | Card et al. | 310/358 X |

FOREIGN PATENT DOCUMENTS 63-78700 4/1988 Japan.

OTHER PUBLICATIONS

"Tailoring the Properties of Composite Piezoelectric Materials for Medical Ultrasonic Transducers" by Smith et al; 1985 Ultrasonics Symposiium; IEEE pp. 642-647.
"Medical Ultrasonic Transducer Using PZT/Polymer Composites" by Nakaya et al; Central Research Laboratory, Hitachi Ltd.

Primary Examiner—Mark O. Budd
Attorney, Agent, or Firm—Lowe, Price, LeBlanc & Becker

[57] ABSTRACT

There is herein disclosed a piezoelectric composite transducer comprising a plurality of piezoelectric ceramic poles. The plurality of piezoelectric ceramic poles are arranged two-dimensionally so as to form spaces therebetween. Organic films are disposed on both end surfaces of the plurality of piezoelectric ceramic poles so that the spaces forms hollow portions. The hollow portions causes making small its acoustic impedance up to a value close to the acoustic impedance of water or a human body.

8 Claims, 2 Drawing Sheets

PIEZOELECTRIC COMPOSITE TRANSDUCER FOR USE IN ULTRASONIC PROBE

BACKGROUND OF THE INVENTION

The present invention relates to a piezoelectric composite transducer or an array of piezoelectric composite transducers of an ultrasonic probe for use in sonars for detection of a target object in water, ultrasonic diagnostic apparatus for examination of a human body and others.

Conventionally, as a material of a piezoelectric transducer used in an ultrasonic probe of a sonar, ultrasonic diagnostic apparatus and others whose investigation subject is water and human bodies, PZT or lead titanate (Pb Ti O$_3$) ceramics is being used because of having a high electro-mechanical coupling factor. However, since these piezoelectric transducer materials have an acoustic impedance of 25 to $35 \times 10^6$ Kg/m$^2$. s which is extremely higher than the acoustic impedance, i.e., about $1.5 \times 10^6$ Kg/m$^2$. s, of the water or human body, mismatch easily occurs to deteriorate the efficiency. Thus, recently, as the piezoelectric transducer material having a high electro-mechanical coupling factor and a low acoustic impedance close to that of the water or human body, a so-called piezoelectric composite transducer material is being studied which is composed of finely-divided piezoelectric ceramics and an organic material filling up spaces between the finely-divided ceramics. In addition, the piezoelectric ceramics is arranged so as to have a porous structure whereby the aforementioned characteristic can be obtained.

One example of the above-mentioned piezoelectric composite transducer are known by "W.A. Smith et al: Proc. IEEE 1985 Ultrasonics Symp. 642-647" or "Electronic Communication Academic Society Technical Research Report Shigaku Giho Vol. 83. No. 160 U.S. 83-30. The conventional piezoelectric composite transducer will be described hereinbelow with reference to FIG. 1.

In FIG. 1, a so-called 1-3 type piezoelectric composite transducer 53 is illustrated where a PZT piezoelectric ceramics 51 and an organic polymeric material 52 such as a silicon rubber and an epoxy resin are one-dimensionally and three-dimensionally coupled to each other. Generally, for manufacturing this piezoelectric composite transducer 53, one piece of piezoelectric ceramics is cut and finely divided by means of a dicing machine or the like so as to provide a reticulate configuration before filling up with the organic polymeric material 52, i.e., a silicon rubber, spaces between the cut piezoelctric ceramics 51. At this time, by adjusting the thickness of the edge for cutting the piezoelectric ceramics 51 and the cutting pitch, the volume ratio of the piezoelectric ceramics 51 is allowed to be controlled so as to attain a desirable characteristic. The electro-mechanical coupling factor of the piezoelectric composite transductor thus arranged can be obtained to be substantially equal to that of a single piezoelectric ceramics and further the acoustic impedance thereof becomes smaller than that of the single piezoelectric ceramics. piezoelectric ceramics 51 to 25% and the organic polymeric material, i.e., silicon rubber, is 75%, the acoustic impedance of the piezoelectric composite transducer 53 becomes about $8.8 \times 10^6$ Kg/m$^2$. s, thereby resulting in considerably improving the matching to the acoustic impedance of water or human body as compared with that of a single piezoelectric ceramics to heighten the transmission and reception efficiency of an ultrasonic wave.

The other conventional piezoelectric transducer using a porus piezoelectric ceramics is known by Japanese Patent Provisional Publication No. 63-78700. In this piezoelectric composite transducer, a PZT piezoelectric ceramics, for example, is arranged so as to have a porous structure to lower the acoustic impedance with decrease in the density. For example, a dispersion liquid is produced with a PZT ceramics powder and a PVA and a water soluble acrylic resin, acting as a binder, and then formed so as to have a sheet-like configuration, before burning with a vacancy rate of member to obtain a porous ceramics with a vacancy rate of 43%. A porous piezoelectric transducer can be obtained by performing the polarization process with respect to the porous ceramics. The acoustic impedance of this porous piezoelectric transducer results in being about $6 \times 10^6$ Kg/m$^2$. s and the electro-mechanical coupling factor thereof becomes about 63%, whereby the acoustic matching with respect to water or a human body becomes excellent as well as the above-mentioned piezoelectric composite transducer to improve the transmission and reception efficiency of an ultrasonic wave.

However, of the above-described conventional examples, the former is arranged as a composited member comprising the piezoelectric ceramics 51 and the organic polymeric material 52, and therefore, the limitation is imposed on approaching the acoustic impedance to that of water or a human body. That is, although the acoustic impedance is expressed as the product of the density and acoustic velocity, in practice the adjustment of the acoustic impedance more depends upon variation of the density rather than the acoustic velocity, and the density of the piezoelectric ceramics 51 is about 7 to 8 Kg/cm$^3$ and the density of the organic polymeric material, i.e., silicon rubber, 52 is about 1 Kg/cm$^3$. Thus, even if the volume ratio of the piezoelectric ceramics 51 is arranged to be small, the acoustic impedance is limited to about $7 \times 10^6$ Kg/m$^2$. s. In the case of further decreasing the volume ratio thereof, the volume ratio of the organic polymeric material 52 should increase, whereby the electro-mechanical coupling factor is lowered so as to deteriorate the entire characteristic thereof. Therefore, when compared with the case of the single piezoelectric ceramics, although the acoustic impedance can be closed to that of water or a human body, there is a problem that the acoustic matching is not yet satisfied. On the other hand, in the case of the latter, although the acoustic impedance can be lowered by increasing the vacancy rate of the porus piezoelectric ceramics, when the vacancy rate exceeds a given value, the mechanical strength becomes extremely weak to make easy damage thereof. Further, since the permittivity becomes extremely small, the electrical impedance becomes high to result in provide a problem that difficulty is encountered to meet the electrical matching. Thus, it is difficult to decrease the acoustic impedance to be smaller than a predetermined value and this cause the acoustic impedance to be difficult to be sufficiently close to the acoustic impedance of water or a human body, thereby resulting in impossibility to sufficiently satisfy the acoustic matching.

SUMMARY OF THE INVENTION

It is therefore an object of the present invention to provide a piezoelectric composite transducer which has a high electro-mechanical coupling factor and further has an acoustic impedance close to that of water or a human body as much as possible to achieve an excellent acoustic matching with respect to the water and human body to improve the transmission and reception efficiency of an ultrasonic wave and which is capable of improving the resolution in the depth direction and widening the frequency band.

In accordance with the present invention, there is provided a piezoelectric composite transducer comprising a plurality of piezoelectric ceramic members, an organic material and hollow portions.

Preferably, each of the plurality of piezoelectric ceramic members has a pole-like configuration and the plurality of piezoelectric ceramic members are arranged two-dimensionally and held by the organic material, the hollow portions being formed in spaces between the plurality of piezoelectric members.

In accordance with the present invention, there is further provided a piezoelectric composite transducer comprising a plurality of porous piezoelectric ceramic members, an organic material and hollow portions.

Preferably, each of the plurality of porous piezoelectric ceramic members has a pole-like configuration and has therein hollows, and the plurality of porous piezoelectric ceramic members are arranged two-dimensionally so as to form spaces therebetween, the spaces being filled up with the organic material.

In accordance with the present invention, there is still provided a piezoelectric composite transducer comprising: a plurality of piezoelectric ceramic poles which are arranged two-dimensionally so as to form spaces therebetween; and at least one organic member disposed on one end surface of the plurality of piezoelectric ceramic poles so that hollow portions are formed by the spaces therebetween.

BRIEF DESCRIPTION OF THE DRAWINGS

The object and features of the present invention will become more readily apparent from the following detailed description taken in conjunction with the accompanying drawings in which.

DETAILED DESCRIPTION OF THE INVENTION

Figure 1:
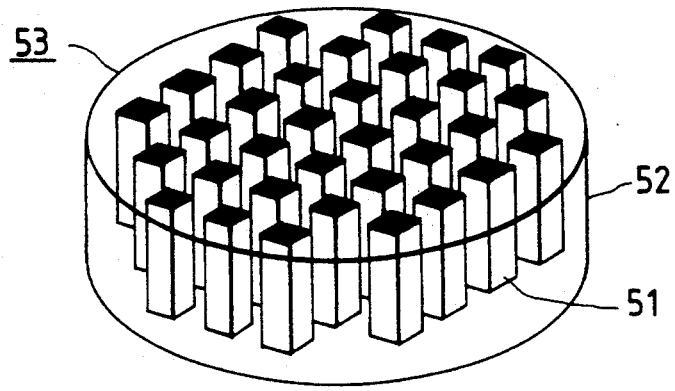
FIG. 1 is a perspective view showing a prior art piezoelectric composite transducer.
Figure 2:
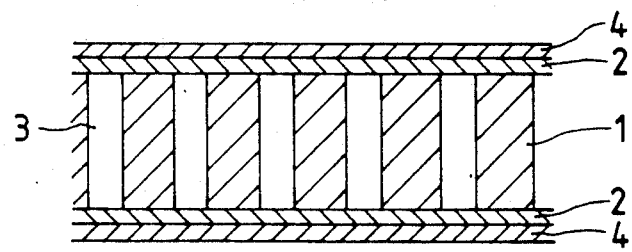
FIGS. 2 through 7 show first to sixth embodiments of a piezoelectric composite transducer according to the present invention.

A first embodiment of the present invention will be described hereinbelow with reference to FIG. 2 which is a cross-sectional view showing a piezoelectric composite transducer of the first embodiment. As illustrated in FIG. 2, a PZT piezoelectric ceramic plate having a desirable thickness is finely divided reticulately so as to form a number of fine pole-like piezoelectric ceramics 1 which are in turn arranged two-dimensionally. These piezoelectric ceramics poles 1 are at both end surfaces sandwiched by self-adhesion type epoxy resin films 2 which are made of an organic polymeric material. The self-adhesion type epoxy resin films 2 are heated under pressure so as to be adhered to the piezoelectric ceramics poles 1 and then cured. Here the self-adhesion type epoxy resin films 2 have a nature that the adhesion is effected in the softened state, thereby fixing the piezoelectric ceramics poles 1 without entering into gaps between the piezoelectric ceramics poles 1. Thus, the gaps therebetween results in forming hollow portions 3. On outer surfaces of the self-adhesion type epoxy resin films 2 are deposited or plated electrodes 4 made of Al, Ag, Au or the like. Lead wires (not shown) are taken out from portions of the electrodes 4. Although not shown, if required, on one of the electrodes 4 is disposed a back loading material and on the other electrode 4 for reflectimg an ultrasonic wave are disposed an acoustic matching layer and an acoustic lens for focusing an acoustic wave.

Here, in forming an ultrasonic probe and transmitting and receiving an ultrasonic wave, the above-described piezoelectric composite transducer is driven in singles or a plurality of the piezoelectric composite transducer are used in an arrayed state.

For manufacturing the piezoelectric composite transducer according to the embodiment of this invention, for example, as the piezoelectric ceramics poles 1 are used a PZT material C-6 (density: 7.4 Kg/m$^3$), having a thickness of 0.5 mm, which is developed by Fuji Ceramics CO., Ltd. The piezoelectric composite transducer is arranged so that the volume ratio of the gap portions, i.e., hollow portions 3, formed by reticulately dividing the PZT material block is 75% and the volume ratio of the piezoelectric ceramic poles 1 is 25%. The density $\rho$ of the piezoelectric composite transducer which is formed by adhering the self-adhesion type epoxy resin films 2 with a thickness of 100 $\mu$m with respect to both wnd surfaces of the piezoelectric ceramic poles 1 can be expressed in accordance with the following equation.

$$\rho = V_1\rho_1 + V_2\rho_2 + V_3\rho_3 \qquad (1)$$

where $V_1$, $\rho_1$ represent the volume ratio and density of the piezoelectric ceramic poles 1, $V_2$, $\rho_2$ designate the volume ratio and density of the self-adhesion type epoxy resin films 2 and $V_3$, $\rho_3$ depict the volume ratio and density of the hollow portion (air) 3.

Thus, the density $\rho$ of the piezoelectric composite transducer results in being about 1.63 Kg/m$^3$ in accordance with the aforementioned equation (1).

Here, in the piezoelectric composite transducer, since air (0.344 Km/s) is included therein, the sound velocity slower than that (3 to 4 Km/s) of the conventional piezoelectric composite transducer which is formed using only the piezoelectric ceramics and epoxy resin, that is, the velocity becomes about 2 Km/s. Therefore, the acoustic impedance of the piezoelectric composite transducer of this embodiment becomes 3 to 4$\times$10$^6$ Kg/m$^2$.s which is considerably close to the acoustic impedance of water or a human body, thereby providing an piezoelectric composite transducer which has a high ultrasonic wave transmission and reception efficiency and which is capable of reducing the reflection with respect to the water or human body, improving the resolution in the depth direction, and widening the frequency band.

Figure 3:
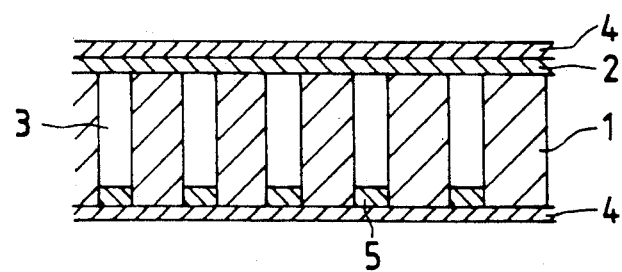

Secondly, a second embodiment of the present invention will be described hereinbelow. FIG. 3 is a cross-sectional view showing an piezoelectric composite transducer according to the second embodiment of this invention.

In FIG. 3, the piezoelectric composite transducer includes two-dimensionally arranged piezoelectric ceramic poles 1 which are formed by finely dividing reticulately a single PZT piezoelectric ceramic plate having a desirable thickness. In this second embodiment, gaps between the piezoelectric ceramic poles 1 is filled up in a manner of casting with a resin 5 which is an organic polymeric material and which is then cured. Thereafter, the resin 5 portion is cut reticulately in the same manner, so that a portion of the resin 5 remains at one end side of the piezoelectric ceramic poles 1. On the end surfaces of the piezoelectric ceramic poles 1 opposite to the resin 5 remaining side is provided a self-adhesion type epoxy resin film 2 which is an organic polymeric material and which heated and cured so as to hold the piezoelectric ceramic poles 1. As well as in the above-mentioned first embodiment, on the other surfaces of the piezoelectric ceramic poles which are at the resin 5 side and further on the outer surface of the self-adhesion type epoxy resin film 2 are disposed electrodes 4, thereby constructing the piezoelectric composite transducer. The other portions are the same structure as the above-mentioned first embodiment.

The piezoelectric composite transducer of this embodiment can have a characteristic similar to that piezoelectric composite transducer of the first embodiment.

Here, it is appropriate to use a porous ceramics for the piezoelectric poles 1 in the first and second embodiments. In this instance, since, in addition to the hollowing portions 3, the porous piezoelectric ceramics itself has hollows, it is possible to make small the acoustic impedance.

Figure 4:
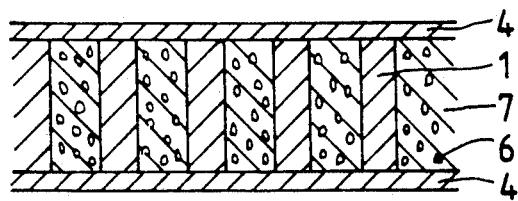

A third embodiment of the present invention will be described hereinbelow. FIG. 4 being a cross-sectional view showing a piezoelectric composite transducer according to the third embodiment of this invention. As illustrated in FIG. 4, a single PZT piezoelectric ceramic plate is reticulately cut to be finely divided so that a number of fine pole-like piezoelectric ceramics are arranged two-dimensionally. In gaps between piezoelectric ceramic poles 1 by casting is filled up a resin 7 including microballoons (hollow members) 6, which is in turn cured so as to hold the piezoelectric ceramic poles 1. As well as in the first embodiment, electrodes 4 are provided on both end surfaces of the piezoelectric ceramic poles 1 and the resin 7 so as to form the piezoelectric composite transducer.

For manufacturing the piezoelectric composite transducer, for example, as the piezoelectric ceramic poles 1 is used a PZT ceramic C-6 (density: 7.4 Kg/m$^3$) developed by Fuji Ceramics CO., Ltd, and as the microballon 6 is used a plastic microballoon F30E developed by Matsumoto Yushi Co., Ltd., and as the epoxy resin 7 is used Epo-tek 301, developed by Epoxy Technology Inc., to which the plastic microballoons F30E of 8% in weight percent are mixed so as to obtain the density of 0.54 Kg/m$^3$ and the acoustic velocity of 1.7 Km/s. The gaps between the piezoelectric ceramic poles 1 filled with the epoxy resin 7 which is in turn heated and cured. In this instance, when the volume ratio of the piezoelectric ceramic poles 1 is 25% and the volume ratio of the epoxy resin 7 including the microballoon 6 is 75%, the density of the piezoelectric composite transducer is about 2.26 Kg/m$^2$. Furthermore, since the microballoons 6 mixed to the epoxy resin 7 so as to form hollows so that the acoustic velocity is slower than that (2.5 to 3 Km/s) of only epoxy resin, the acoustic velocity of the piezoelectric composite transducer of this embodiment results in becoming slower that of the conventional piezoelectric composite transducer comprising only the piezoelectric ceramic s and epoxy resin. Thus, the acoustic impedance of the piezoelectric composite transducer of this embodiment becomes about $5 \times 10^6$/m$^2$.s which can be reduced by about 20% as compared with that of the conventional piezoelectric composite transducer comprising only the piezoelectric ceramics and silicon rubber. As a result, the acoustic impedance can be close to that of water or a human body, thereby attaining an piezoelectric composite transducer having an excellent transmission and reception efficiency with respect to an ultrasonic wave. In addition, the piezoelectric composite transducer has a characteristic similar to that of the first embodiment.

Here, although in this embodiment the epoxy resin is used as the resin 7 for filling up the gaps between the piezoelectric ceramic poles 1, it is also appropriate to use other polymeric materials such as polyurethane and synthetic rubber. Further, a porous piezoelectric ceramics can be used for the piezoelectric ceramic poles 1. In this case, the acoustic impedance can be further reduced because the porous piezoelectric ceramics itself has hollows in addition to the hollows due to the microballons 6. Still further, it is possible to use various types of microballoons such as glass-made microballons, carbon-made microballoons and silas instead of the plastic microballoons.

A fourth embodiment of the present invention will be described hereinbelow, FIG. 5 being a cross-sectional view showing an piezoelectric composite transducer according to the fourth embodiment of this invention.

Figure 5:
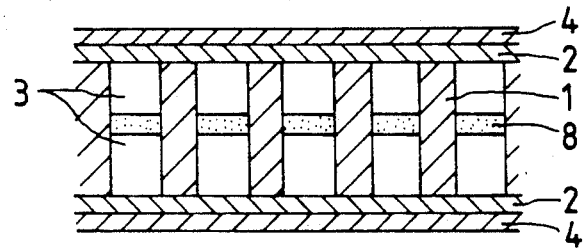

As illustrated in FIG. 5, a single piezoelectric ceramic plate having a desirable thickness is reticulately cut to be finely divided so as to form a number of piezoelectric composite ceramic poles 1 which are in turn arranged two-dimensionally. Gaps formed between the piezoelectric ceramic poles 1 are filled with an epoxy resin 8, being an organic polymeric material, which is in turn cured. Thereafter, the epoxy resin 8 is cut to be removed from both sides so that portions of the epoxy resin 8 remain at the center portions. Further, the piezoelectric ceramic poles 1 are sandwiched by self-adhesion type epoxy resin films 2 from both end surfaces thereof. The self-adhesion type epoxy resin films 2 are heated under pressure so as to be adhered to the piezoelectric ceramic poles 1 which are in turn held thereby. As a result, hollowing portions 3 are formed between the epoxy resin 8 and the self-adhesion type epoxy resin films 2. Electrodes 4 are provided on the outer surfaces of the self-adhesion type epoxy resin films 2, thereby making up the piezoelectric composite transducer. The other arrangement is similar to that of the first embodiment.

This embodiment can provide a characteristic similar to that of the first embodiment, and since the piezoelectric ceramic poles 1 are bridged by the epoxy resin 8 so as to be reinforced, the mechanical strength of the piezoelectric composite transducer can be improved to heighten the reliability.

Here, although in this embodiment the epoxy resin 8 is used as an organic material for filling up portions of the gaps between the piezoelectric ceramic poles 1, it is also appropriate to use other organic materials such as polyurethane, foaming epoxy resin and foaming polyurethane. In addition, it is possible to use a porous piezoelectric ceramics as the piezoelectric ceramics. In this case, the acoustic impedance can be further reduced due to the hollows of the porous piezoelectric ceramics in addition to the hollowing portions 3 between the piezoelectric ceramic poles 1.

A fifth embodiment of the present invention will be described hereinbelow, FIG. 6 being a cross-sectional view showing an piezoelectric composite transducer according to the fifth embodiment of this invention.

Figure 6:
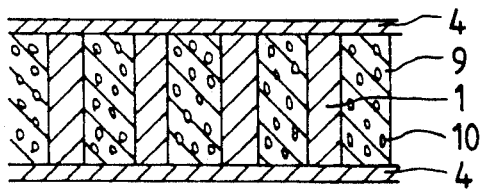

As illustrated in FIG. 6, a single PZT piezoelectric ceramic plate is reticulately cut so as to be finely divided to form a number of piezoelectric ceramic poles which are arranged two-dimensionally. In gaps between the piezoelectric ceramic poles 1 is casted and filled up a foaming polyurethane resin 9, for example, ECCOFOAM FPH/12-10H (density: 0.22 Kg/m$^3$) developed by Grace Japan Co., Ltd. After being cured, hollows 10 are formed in the foaming polyurethane resin 9. Electrodes 4 are disposed on the end surfaces of the piezoelectric ceramic poles 1 and polyurethane resin 9, thereby making up the piezoelectric composite transducer. The other arrangement is similar to that of the first embodiment.

In this embodiment, since the foaming polyurethane resin 9 is used, the density can be reduced due to the hollows 10. Thus, the acoustic impedance can be reduced so as to obtain the piezoelectric composite transducer with an excellent transmission and reception efficiency of an ultrasonic wave. In addition, the piezoelectric composite transducer can have a characteristic similar to that of the first embodiment.

Here, although in this embodiment the foaming polyurethane resin 9 is used, it is also possible to use a foaming polymeric material such as foaming silicon rubber, for example, Tosfoam 5300 (density: 0.25 kg/m$^3$) developed by Toshiba Silicon Co., Ltd. Further, it is possible to use a porous piezoelectric ceramics for the piezoelectric ceramic poles 1. In this instance, the acoustic impedance can be made smaller due to the hollows of the porous piezoelectric ceramics itself in addition to the hollows 10 of the foaming epoxy resin 9.

Furthermore, a sixth embodiment of the present invention will be described hereinbelow, FIG. 7 being a cross-sectional view showing a piezoelectric composite transducer according to the sixth embodiment of this invention.

Figure 7:
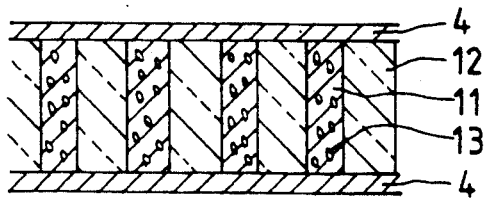

In FIG. 7, a single PZT porous piezoelectric ceramic plate having a desirable thickness is cut reticulately so as to be finely divided to form a number of porous piezoelectric ceramic poles 11 which are arranged two-dimensionally. An epoxy resin 12, being an organic material, is charged in gaps between the porous piezoelectric ceramic poles 11 and cured so as to hold the piezoelectric ceramic poles 11. Electrodes 4 are provided on the end surfaces of the porous piezoelectric ceramic poles 11 and epoxy resin 12 so as to make up the piezoelectric composite transducer in which the porous piezoelectric ceramic poles itself 11 have hollows 13. The other arrangement is similar to that of the first embodiment. The density of the porous piezoelectric ceramic poles can be adjusted with hollowing rate. For example, when a PZT ceramics is used and the hollowing rate is about 40%, the density becomes about 3.8 kg/m$^3$ and the acoustic impedance becomes about $6 \times 10^6$ kg/m$^2$. s. In the case that the volume percents of such a porous piezoelectric ceramic poles 11 and the epoxy resin 12 are 25% and 75%, the density of the piezoelectric composite transducer becomes about 1.78 kg/m$^3$. Thus, the acoustic impedance becomes below $5 \times 10^6$ kg/m$^2$. s which is smaller than that of a conventional piezoelectric transducer using a single porous piezoelectric ceramics and which is closer to the acoustic impedance of water or a human body, thereby attaining a piezoelectric composite transducer with an excellent transmission and reception efficiency of an ultrasonic wave. The piezoelectric composite transducer of this embodiment has a characteristic similar to that of the first embodiment.

Here, although in this embodiment the epoxy resin is used as a material for filling up the gaps between the porous piezoelectric ceramic poles 11, it is also possible to use an organic material such as synthetic rubber and polyurethane and, if using a foaming organic material such as foaming epoxy resin and foaming polyurethane, it is possible to form hollows in the organic material.

With the aforementioned arrangement, the density can be reduced and further the acoustic impedance can be made smaller so as to be as closer as possible to that of water and a human body. Accordingly, when being used for an ultrasonic probe, the transmission and reception of an ultrasonic wave can be effected with a high efficiency. In addition, as described above, the acoustic impedance becomes close to that of the water and human body and hence the reflection between the piezoelectric composite transducer and the water or human body can be reduced to improve the resolution in the depth direction and to widen the frequency band. When using such a piezoelectric composite transducer for an ultrasonic probe of an ultrasonic diagnostic apparatus, it is possible to obtain a high-resolution ultrasonic image with a high efficiency.

It should be understood that the foregoing relates to only preferred embodiments of the invention, and that it is intended to cover all changes and modifications of the embodiments of the invention herein used for the purposes of the disclosure, which do not constitute departures from the spirit and scope of the invention.

What is claimed is:

1. A piezoelectric composite transducer comprising a plurality of pole-shaped porous piezoelectric ceramic members arranged two-dimensionally so as to form gaps therebetween, a first organic film provided on one end of the two-dimensionally arranged ceramic members, and a second organic film provided on the other end of the two-dimensionally arranged ceramic members, whereby said gaps between the two-dimensionally arranged ceramic members are sealed with said first and second organic films so that said piezoelectric composite transducer has a plurality of hollow portions therein.

2. A piezoelectric composite transducer comprising a plurality of pole-shaped porous piezoelectric ceramic members arranged two-dimensionally so as to form gaps therebetween, an organic film provided on at least one end of the two-dimensionally arranged ceramic members, and an organic material with which said gaps are partially filled so as to be sealed with said organic film and said organic material so that said piezoelectric composite transducer has a plurality of hollow portions therein.

3. A piezoelectric composite transducer as claimed in claim 1, wherein said first and second organic films are made of a member selected from the group consisting of synthetic rubber, epoxy resin and polyurethane resin.

4. A piezoelectric composite transducer as claimed in claim 2, wherein said organic film and said organic material is made of a member selected from the group consisting of synthetic rubber, epoxy resin and polyurethane resin.

5. A piezoelectric composite transducer comprising a plurality of pole-shaped piezoelectric ceramic members arranged two-dimensionally so as to form gaps therebetween, said gaps being filled with an organic material which includes microballoons.

6. A piezoelectric composite transducer as claimed in claim 5, wherein said organic material is made of a member selected from the group consisting of synthetic rubber, epoxy resin and polyurethane resin.

7. A piezoelectric composite transducer as claimed in claim 6, wherein said pole-shaped piezoelectric ceramic members are pole-shaped porous piezoelectric ceramic members.

8. A piezoelectric composite transducer as claimed in claim 5, wherein said microballoons are made of a member selected from the group consisting of plastic, glass, carbon and silas.

* * * * *